(12) United States Patent
Butler et al.

(10) Patent No.: US 8,221,467 B2
(45) Date of Patent: Jul. 17, 2012

(54) DYNAMIC SPINAL STABILIZATION DEVICE AND SYSTEMS

(75) Inventors: Michael S. Butler, St. Charles, IL (US); Michael J. Milella, Jr., Schaumburg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 612 days.

(21) Appl. No.: 11/601,472

(22) Filed: Nov. 17, 2006

(65) Prior Publication Data

US 2007/0118122 A1 May 24, 2007

Related U.S. Application Data

(60) Provisional application No. 60/738,380, filed on Nov. 18, 2005.

(51) Int. Cl.
*A61B 17/70* (2006.01)
(52) U.S. Cl. ........................ 606/257; 606/255
(58) Field of Classification Search .............. 606/246, 606/254–257, 259–264, 277, 251, 253; 623/17.11, 623/17.13, 17.15, 17.16; 403/343
See application file for complete search history.

(56) References Cited

U.S. PATENT DOCUMENTS

| | | | |
|---|---|---|---|
| 4,041,939 A | 8/1977 | Hall | |
| 4,804,000 A | 2/1989 | Lamb et al. | |
| 5,034,011 A * | 7/1991 | Howland | 606/256 |
| 5,047,029 A * | 9/1991 | Aebi et al. | 606/264 |
| 5,466,238 A * | 11/1995 | Lin | 606/264 |
| 6,241,730 B1 * | 6/2001 | Alby | 606/256 |
| 6,290,700 B1 * | 9/2001 | Schmotzer | 606/263 |

(Continued)

FOREIGN PATENT DOCUMENTS

FR 2715825 8/1995

(Continued)

OTHER PUBLICATIONS

PCT International Search Report related to International Application No. PCT/US06/44914, date of mailing of the International Search Report, Aug. 20, 2007 (3 pgs.).

*Primary Examiner* — Eduardo C Robert
*Assistant Examiner* — Jerry Cumberledge
(74) *Attorney, Agent, or Firm* — Foley & Lardner LLP

(57) ABSTRACT

A dynamic spine stabilization element of a spine stabilization assembly includes first and second spinal rod segments that are coupled to one another via a connector. The connector allows movement of a spinal rod segment with respect to the coupling device and/or with respect to another spinal rod segment. This provides limited angulation (e.g. bending) between spinal rod segments allowing for limited movement of the vertebra connected by the present dynamic stabilization element. The connector may allow pivoting motion of the rod segments relative to the coupling device and relative to the other rod segment such as pivoting motion of one rod segment in a first plane and pivoting motion of the other rod segment in a second plane that is perpendicular to the first plane. The connector may also be bendable or flexible. In this form, the connector allows limited flexing, bending or angulation as between the associated spinal rod segments during use. Moreover, ends of the spinal rod segments may be configured to prevent or limit rotation of the spinal rod segments. The configured ends may cooperate with the coupling device to achieve the limitation on rotational movement.

9 Claims, 15 Drawing Sheets

U.S. PATENT DOCUMENTS

| | | |
|---|---|---|
| 6,736,818 B2 * | 5/2004 | Perren et al. ............... 606/63 |
| 7,326,210 B2 * | 2/2008 | Jahng et al. ............... 606/86 A |
| 7,556,639 B2 * | 7/2009 | Rothman et al. ............... 606/257 |
| 7,621,940 B2 * | 11/2009 | Harms et al. ............... 606/257 |
| 7,815,665 B2 | 10/2010 | Jahng et al. |
| 2004/0039384 A1 | 2/2004 | Boehm, Jr. et al. |
| 2005/0038432 A1 * | 2/2005 | Shaolian et al. ............... 606/61 |
| 2005/0065514 A1 * | 3/2005 | Studer ............... 606/61 |
| 2005/0085815 A1 * | 4/2005 | Harms et al. ............... 606/61 |
| 2005/0113927 A1 | 5/2005 | Malek |
| 2005/0124991 A1 * | 6/2005 | Jahng ............... 606/61 |
| 2005/0131407 A1 * | 6/2005 | Sicvol et al. ............... 606/61 |
| 2005/0143823 A1 | 6/2005 | Boyd et al. |
| 2005/0165396 A1 * | 7/2005 | Fortin et al. ............... 606/61 |
| 2005/0182409 A1 | 8/2005 | Callahan et al. |
| 2005/0222569 A1 * | 10/2005 | Panjabi ............... 606/61 |
| 2006/0036240 A1 * | 2/2006 | Colleran et al. ............... 606/61 |
| 2006/0106381 A1 * | 5/2006 | Ferree et al. ............... 606/61 |
| 2006/0229612 A1 * | 10/2006 | Rothman et al. ............... 606/61 |
| 2006/0264935 A1 | 11/2006 | White |
| 2006/0264937 A1 * | 11/2006 | White ............... 606/61 |
| 2007/0118122 A1 | 5/2007 | Butler et al. |

FOREIGN PATENT DOCUMENTS

| | | |
|---|---|---|
| FR | 2715825 A1 * | 8/1995 |
| WO | WO-2009/026519 | 2/2009 |

* cited by examiner

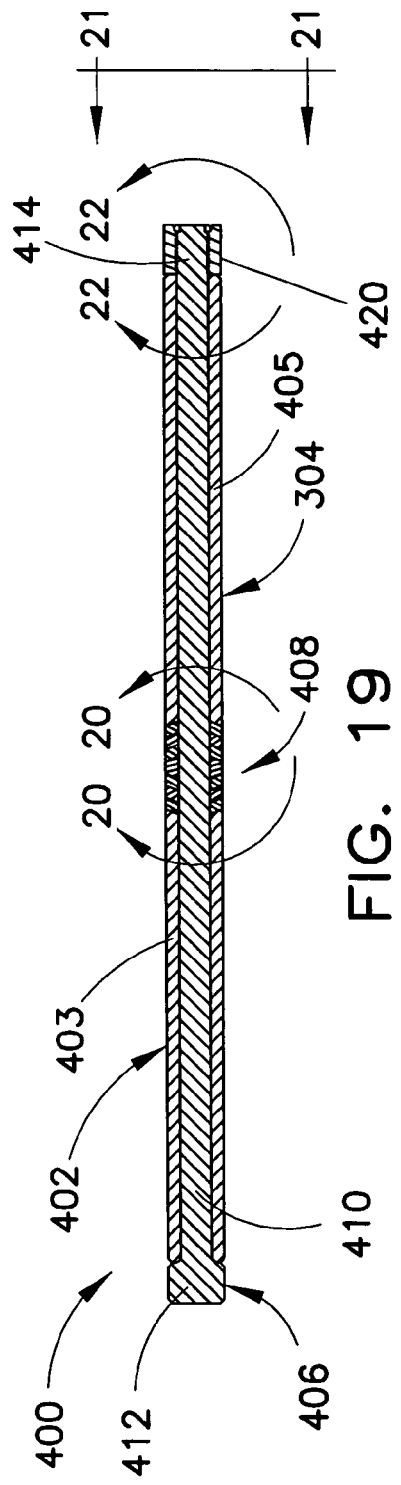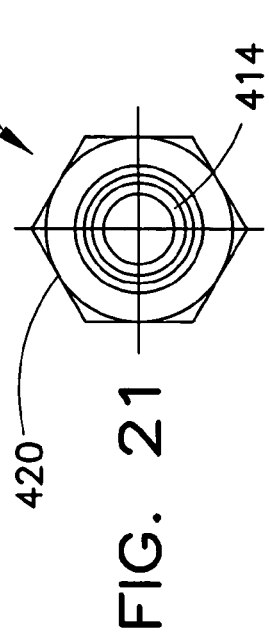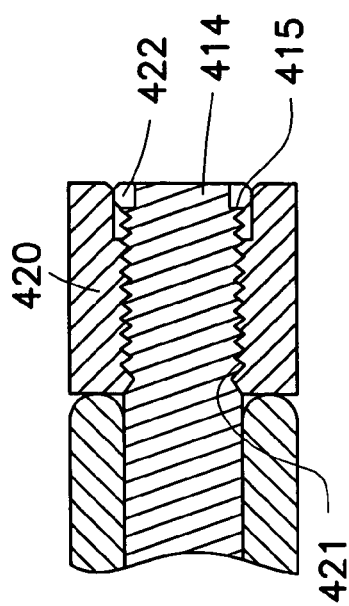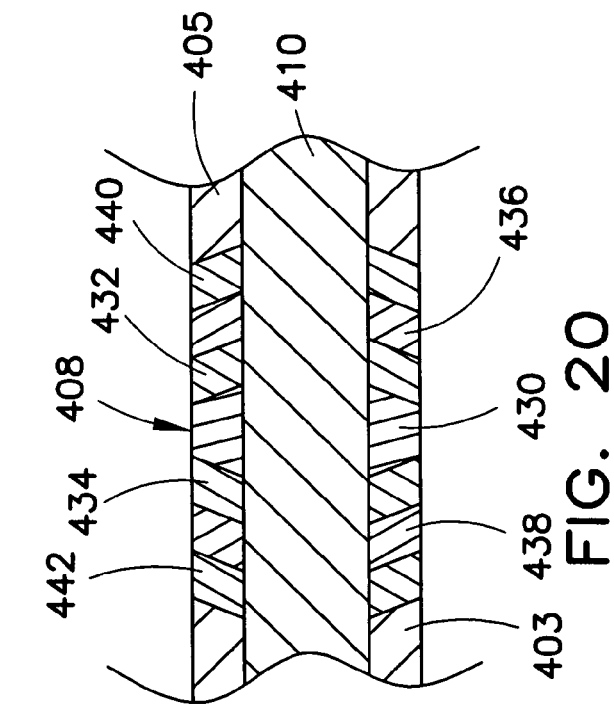

DYNAMIC SPINAL STABILIZATION DEVICE AND SYSTEMS

RELATED APPLICATIONS

This patent application claims the benefit of and/or priority to U.S. Provisional Patent Application No. 60/738,380 filed Nov. 18, 2005, entitled "Dynamic Spinal Stabilization Devices and Systems" the entire contents of which is specifically incorporated herein by reference.

BACKGROUND

1. Field of the Invention

The present invention provides devices for the stabilization of the spinal column and, more particularly, to dynamic devices for the stabilization of the spinal column.

2. Background Information

A significant portion of the population suffers from spinal problems. Such spinal problems may be attributable to disease, trauma and/or other event. In the case of degenerative disc disease, spinal trauma and the like, such conditions are often painful and/or physically deforming. Depending on the situation, the pain and complications caused by these conditions may require that one or more vertebra, facet joints, and/or intervertebral discs be removed from the spinal column. In these procedures, bone fusion is a common treatment used to facilitate the realignment and/or fixation of the remaining spinal elements.

Currently, two types of systems or assemblies are utilized for securing and/or stabilizing one or more vertebrae in order to achieve bone fusion. One type of spine stabilizing assembly generally includes two posterior vertebral plates disposed longitudinally on either side of the spinous processes. Each plate is attached between adjacent vertebra using bone anchoring elements, such as bone screws. Together, the plates provide a rigid vertebral fixation.

Another type of spine stabilizing assembly generally includes two posterior vertebral rods disposed longitudinally on either side of the vertebrae (e.g. the spinous processes thereof). Like the plates, these rods are attached between adjacent vertebrae using appropriate bone anchoring devices to achieve rigid vertebral fixation.

These spine stabilizing assemblies are also used to correct spinal deformities such as scoliosis or the like. For this use, such spine stabilizing assemblies may have spine rods that span two or more vertebrae.

A drawback of rigid fixation relates to the loading that occurs on the stabilizing assemblies and especially on the anchoring sites during normal activity. These loads may result in loosening of the assembly from the vertebrae or even breaking of the assembly. Also, fusion subjects the non-fused spine elements to various stresses, particularly the remaining adjacent vertebrae and vertebral discs since these elements must accommodate different degrees of motion. Moreover, spinal fusion limits the range of a patient's motion.

Because of the drawbacks to rigid spine fixation systems, semi-rigid spine fixation systems have been proposed that aim to allow limited intervertebral movement for promoting bone fusion and/or reducing spine stress. These semi-rigid spine fixation systems, however, are far from effective and/or efficient.

There is thus a need for an improved semi-rigid spine stabilization device, assembly and/or system.

This need and others is accomplished through application of the principles of the subject invention and/or as embodied in one or more various forms and/or structures such as are shown and/or described herein.

SUMMARY OF THE INVENTION

The present invention provides dynamic spine stabilization elements, systems, assemblies and/or devices particularly, but not necessarily, for posterior spine stabilization.

A dynamic spine stabilization element of a spine stabilization system or assembly, includes first and second spinal rods or rod segments that are coupled to one another via a coupling device. The coupling device provides movement or motion of one or more of the spinal rod segments with respect to the coupling device and/or with respect to the other spinal rod segment. The present invention thus provides spinal stabilization elements for spinal stabilization systems that allow for limited angulation (e.g. bending) between spinal rod segments of the spinal stabilization element. This allows for limited movement of the vertebra connected by the present dynamic stabilization element.

In one form the first and second spinal rod segments are connected via a coupling device that allows pivoting motion of the rod segments relative to the coupling device and relative to the other rod segment. Particularly, the coupling device allows pivoting motion of one rod segment in a first plane and pivoting motion of the other rod segment in a second plane that is perpendicular to the first plane.

In another form, the first and second spinal rod segments are connected via a bendable or flexible coupling device. The coupling device is adapted to allow limited flexing, bending or angulation as between the associated spinal rod segments during use. Particularly, the coupling device allows for 360° angulation.

Ends of the spinal rod segments may be configured to prevent or limit rotation of the spinal rod segments. The configured ends may cooperate with the coupling device to achieve the limitation on rotational movement. In another form, the coupling device and/or the configured ends of the spinal rod segments, allow for limited axial movement between rod segments.

The spinal rod segments may be straight or curved and may be made in different lengths. Spinal rods of various curvatures may also be provided. A stabilization system may include straight and curved spinal rod segments.

BRIEF DESCRIPTION OF THE DRAWINGS

The features and objects of this invention, and the manner of attaining them, will become more apparent and the invention itself will be better understood by reference to the following description of embodiments of the present invention taken in conjunction with the accompanying drawings, wherein:

FIG. 19 is a sectional view another embodiment of a dynamic spinal stabilization element fashioned in accordance with the present principles;

FIG. 20 is an enlarged sectional view of a portion of the dynamic spinal stabilization element of FIG. 19 taken along circle 20-20 of FIG. 19;

FIG. 21 is an end view of the dynamic spinal stabilization element of FIG. 19 taken along line 21-21 of FIG. 19;

FIG. 22 is an enlarged sectional view of a portion of the dynamic spinal stabilization element of FIG. 19 taken along circle 22-22 of FIG. 19;

DETAILED DESCRIPTION OF EMBODIMENTS

Figure 1:
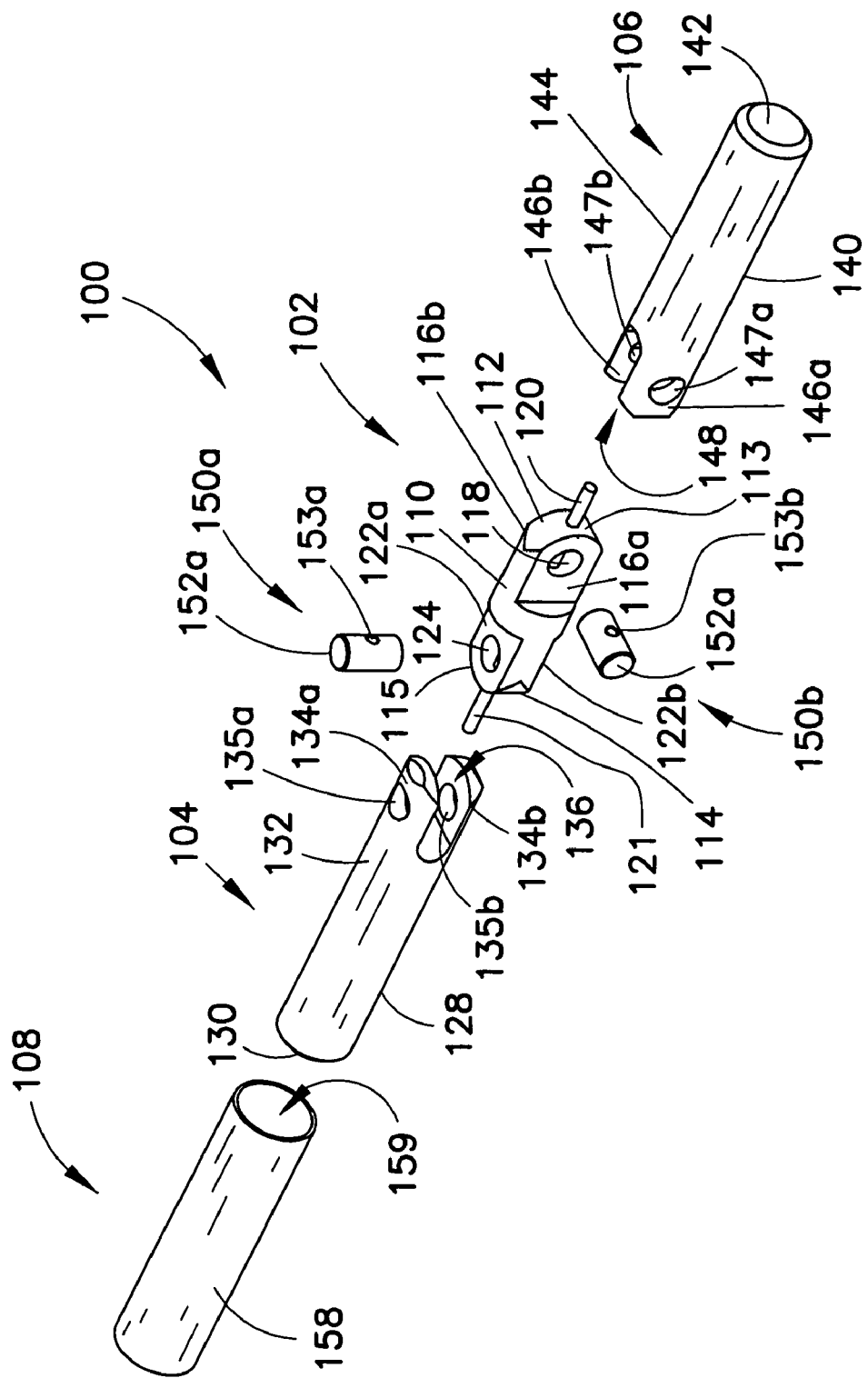
FIG. 1 is an exploded perspective view of an embodiment of a dynamic spinal stabilization element fashioned in accordance with the present principles.

FIG. 1 depicts an exploded view of an embodiment of a dynamic spinal stabilization element or construct generally designated 100 especially for use in a spinal stabilization system or assembly. The dynamic spinal stabilization element 100 is a rod assembly that is designed to be retained at both ends to bone anchoring elements such as bone screws (see e.g. FIGS. 23-26) of the spinal stabilization assembly. The dynamic spinal stabilization element 100 allows motion or movement relative to first and second rods or rod segments 104 and 106. Particularly, the dynamic spinal stabilization element 100 allows motion or movement of the rod segments 104, 106 in two planes of motion, the two planes of motion being perpendicular to one another. The dynamic spinal stabilization element 100 provides a jointed spinal rod.

The dynamic spinal stabilization element 100 has a coupling element 102 that provides jointed coupling or attachment to the rod segments 104, 106. The coupling element 102 is formed of a bio-compatible material of a suitable material strength such as titanium. The coupling element 102 has a generally cylindrical body 110 formed with a first configured end 112 and a second configured end 114. The first configured end 112 includes a rounded nose 113 and first and second flats 116a, 116b that are disposed diametrically opposite one another. A bore 118 is formed in the configured end 112 that extends between the flats 116a, 116b and having an axis that is generally perpendicular to the plane of the flats 116a, 116b. The second configured end 114 includes a rounded nose 115 and first and second flats 122a, 122b that are disposed diametrically opposite one another. A bore 124 is formed in the configured end 114 that extends between the flats 122a, 122b and having an axis that is generally perpendicular to the plane of the flats 122a, 122b.

The first rod segment 104 is formed of a bio-compatible material of a suitable material strength such as titanium and is characterized by a generally cylindrical body 128 of any appropriate length and/or diameter. The body 128 defines a first end 130 and a second end 132. The first end 130 is adapted for reception by a retention device of a spinal stabilization assembly, while the second end 132 is adapted for connection with the coupling element 102.

As such, the second end 132 has first and second prongs or flanges 134a, 134b that define a reception area (slot) 136 therebetween. The edges of the flanges 134a, 134b are rounded or "squared off." Each prong 134a, 134b also includes a bore 135a, 135b, respectively, each having an axis that is generally perpendicular to an axis of the body 128. The slot 136 is sized to receive the end 114 of the coupling element 102 and, particularly, the flats 122a, 122b between the prongs 134a, 134b such that the bore 124 aligns with the bores 135a, 135b. A pivot pin 150a extends through the bores 134a, 124, 135b upon assembly. An elongated retaining pin 121 extends into a bore 153a of the pivot pin 150a and into the body 128.

Figure 2:
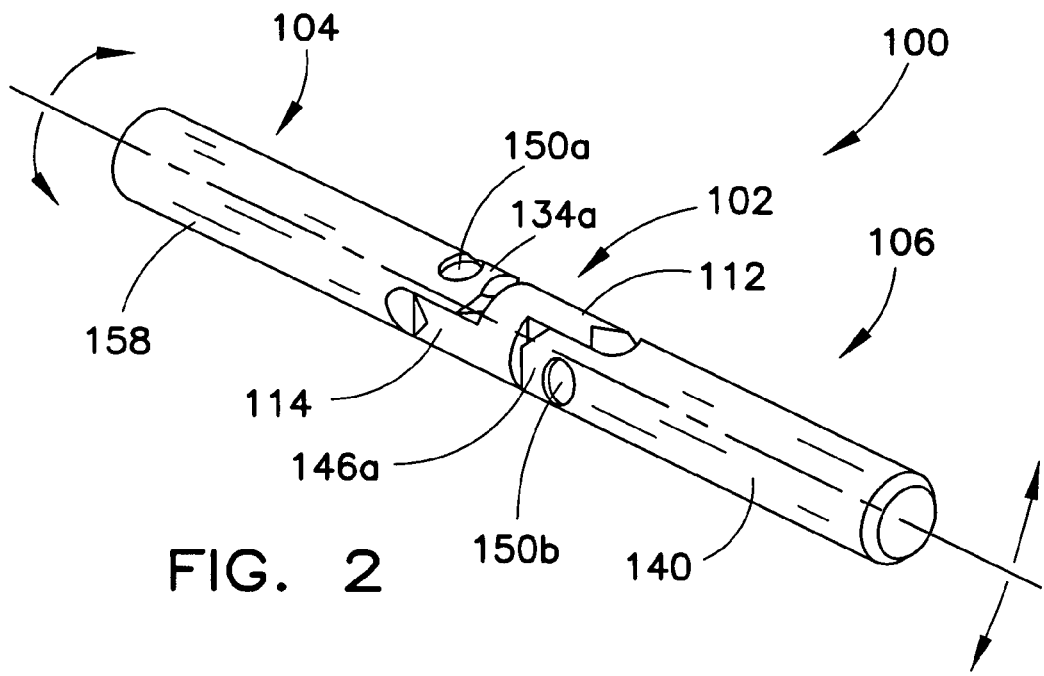
FIG. 2 is a perspective view of the dynamic spinal stabilization element of FIG. 1 assembled but with a sleeve portion removed.

In this manner, the rod segment 104 may pivot about an axis defined by the pivot pin 150a (relative to the coupling element 102) or vice versa. This is illustrated in FIG. 2 by the double-headed arrow about an axis of the rod segment 104 particularly in a plane about the axis thereof. The elongated retaining pin 121 may be of various flexibilities to limit or control the extent of or force required for pivoting movement.

The second rod segment 106 is formed of a bio-compatible material of a suitable material strength such as titanium and is characterized by a generally cylindrical body 140 of any appropriate length and/or diameter. The body 140 defines a first end 142 and a second end 144. The first end 142 is adapted for reception by a retention device of a spinal stabilization assembly, while the second end 144 is adapted for connection with the coupling element 102.

As such, the second end 144 has first and second prongs or flanges 146a, 146b that define a reception area (slot) 148 therebetween. The edges of the flanges 146a, 146b are rounded or "squared off." Each prong 146a, 146b also includes a bore 147a, 147b, respectively, each having an axis that is generally perpendicular to an axis of the body 140. The slot 148 is sized to receive the end 112 of the coupling element 102 and, particularly, the flats 116a, 116b between the prongs 146a, 146b such that the bore 118 aligns with the bores 147a, 147b. A pivot pin 150b extends through the bores 147a, 118, 147b upon assembly. An elongated retaining pin 120 extends into a bore 153b of the pivot pin 150b and into the body 140.

In this manner, the rod segment 106 may pivot about an axis defined by the pivot pin 150b (relative to the coupling element 102) or vice versa. This is illustrated in FIG. 2 by the double-headed arrow about an axis of the rod segment 106 particularly in a plane about the axis thereof. The elongated retaining pin 120 may be of various flexibilities to limit or control the extent of or force required for pivoting movement.

Figure 4:
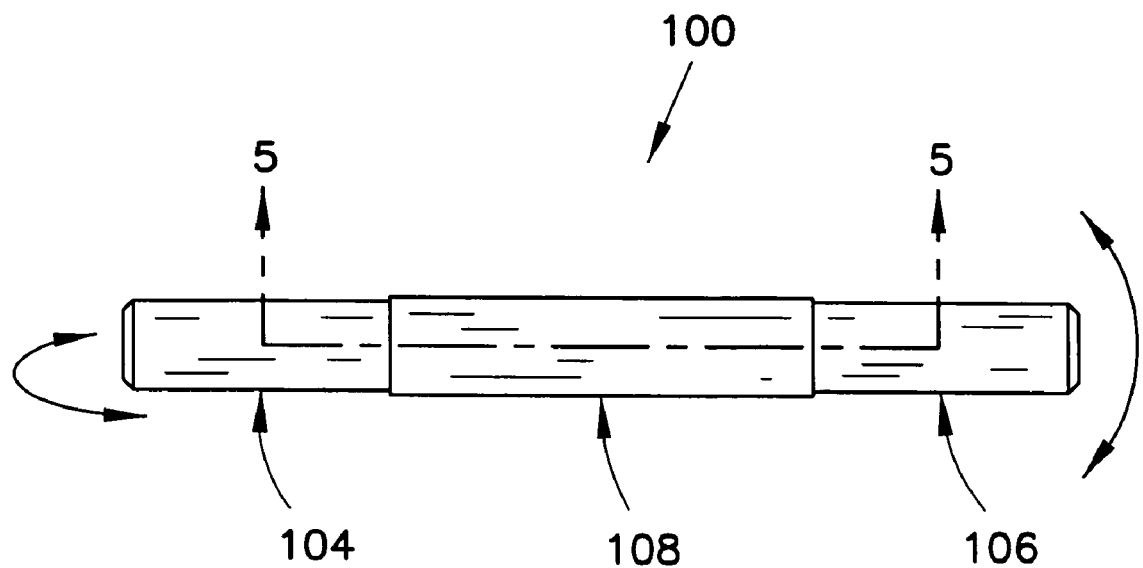
FIG. 4 is a side view of the dynamic spinal stabilization element of FIG. 1 assembled.

A sleeve, covering or the like 108 may be provided as part of the dynamic stabilization element 100. The sleeve 108 is formed by a generally tubular body 158 having a tubular chamber 159. The diameter of the sleeve 108 is sized to be received over and snugly fit onto the rod segments 104, 106 and coupling element 102. FIG. 4 depicts the dynamic stabilization element 100 of FIG. 1 in an assembled form. Again, the double headed arrows illustrate the angulation of the device. The sleeve 108 is formed of a bio-compatible material of a suitable material strength having an appropriate elasticity to allow the pivoting, motion or movement of the assembly joint. In one form, PEEK of a durometer that will allow for angulation (bending or twisting) is used for the sleeve 108.

Figure 5:
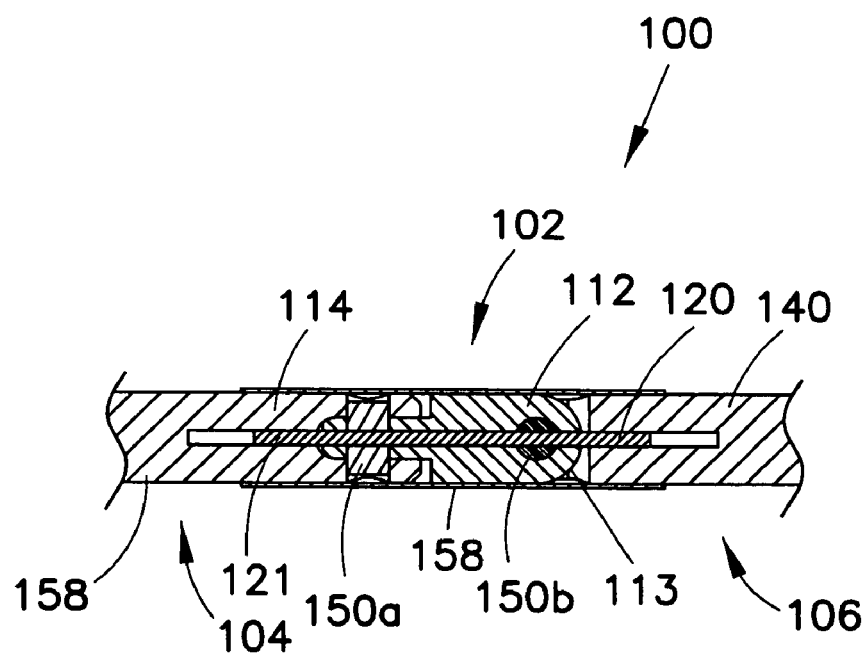
FIG. 5 is a sectional view of a portion of the dynamic spinal stabilization element of FIG. 4 taken along line 5-5 thereof.

FIG. 5 depicts a sectional view of the joint defined by the coupling element 102 and the first and second rod segments 104, 106. It can be appreciated that the elongated retaining pins 120, 121 flex with pivoting of the respective rod segment 106, 104. The stiffer the retaining pin (less flexible), the greater the resistance to pivoting of the rod segment (more force is required to overcome the modulus of the material and thus provide flexure thereof). Conversely, the less stiff the retaining pin (more flexible), the less the resistance to pivoting of the rod segment (less force is required to overcome the modulus of the material and thus provide flexure thereof).

Figure 3:
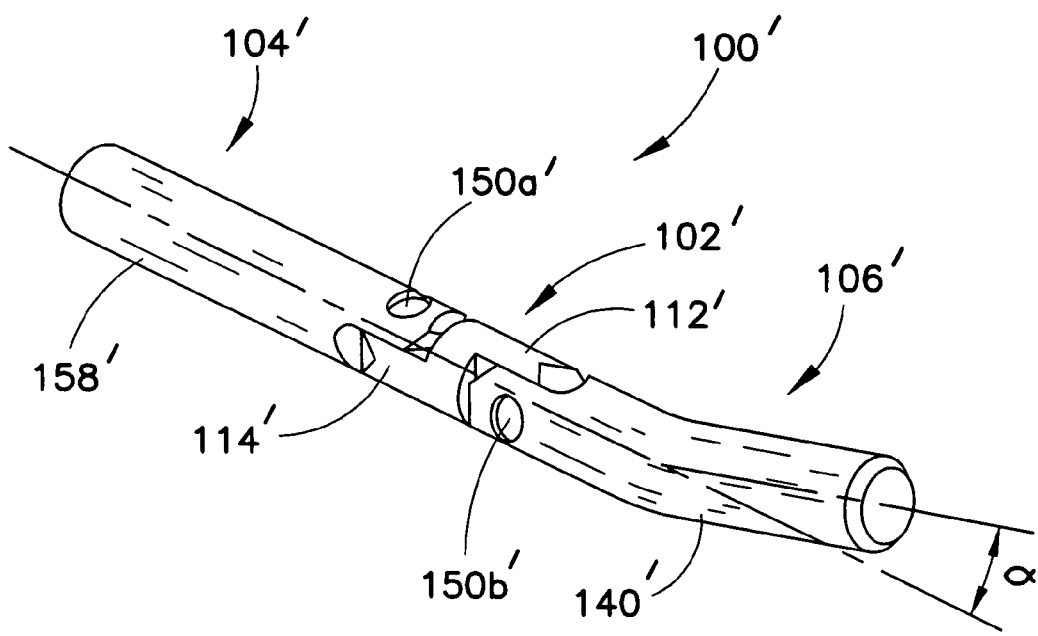
FIG. 3 is a perspective view of an alternative embodiment of the dynamic spinal stabilization element of FIG. 2 assembled but with a sleeve portion removed.

FIG. 3 depicts an alternative embodiment of the dynamic stabilization element 100 of FIG. 1. In particular, the dynamic stabilization element 100 of FIG. 1 utilizes straight rod segments. FIG. 3 illustrates a dynamic stabilization element 100' that utilizes a curved or bent rod segment 106'. The degree of curvature may vary as appropriate as well as the direction of curvature relative to the pivot axis of the coupling element 102' and rod segment 106'. While only one (106') of the two rod segments 104', 106' of the dynamic stabilization element 100' is curved, it should be appreciated that the other rod segment (104') may be curved. The curvature characteristics of each rod segment may be the same or different depending on the application.

Figure 6:
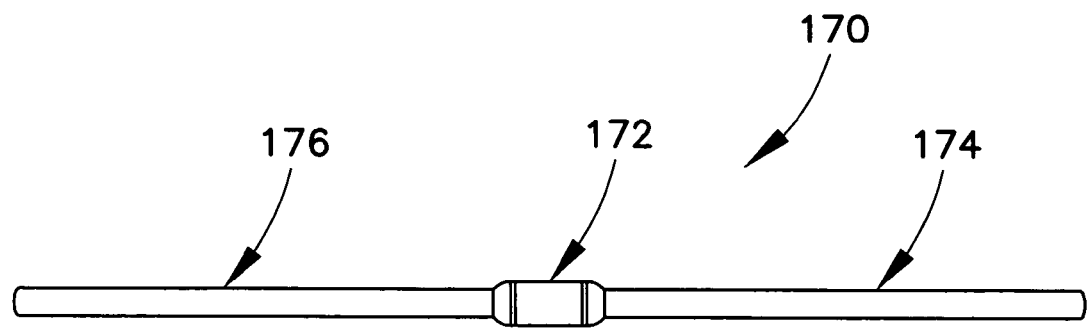
FIG. 6 is a side view of an embodiment of a dynamic spinal stabilization element fashioned in accordance with the present principles.

Referring now to FIG. 6, there is depicted another embodiment of a dynamic stabilization element generally designated 170. The dynamic stabilization element 170 is characterized by first and second spine rods 174, 176 and a coupling element 172. The spine rods 174, 176 are adapted to be received by bone attachment assemblies, particularly at ends distal to the coupling element 172, such that the coupling element 172 is disposed between the bone attachment assemblies. The coupling element 172 is adapted to allow limited bending or angulation as between the rods 174, 176.

The dynamic stabilization element 170 is designed to allow angulation in any plane off of (relative to) the axis of the rod (defined as a cone about the axis of the rod). This allows the dynamic rod element 170 to be installed without regard to rotational orientation (which may be necessary for the dynamic stabilization element 100 of FIG. 1).

Figure 7:
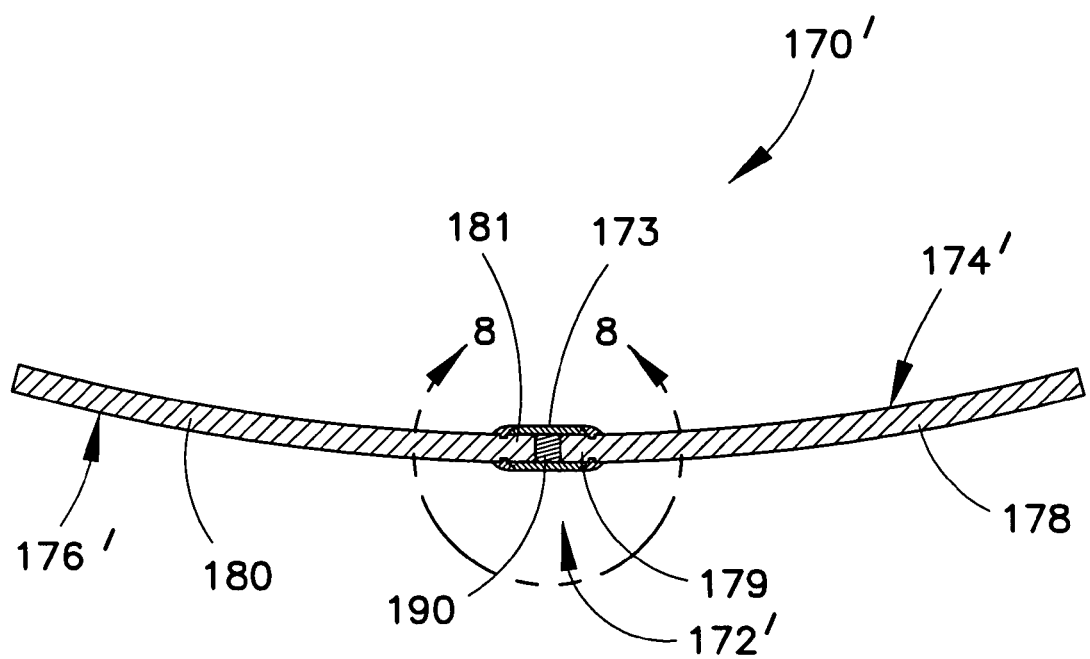
FIG. 7 is a sectional view of a form of the embodiment of the dynamic spinal stabilization element as shown in FIG. 6.

Referring to FIG. 7, there is depicted a cross-sectional view of a form of the dynamic stabilization element 170 of FIG. 6, generally designated 170'. The dynamic stabilization element 170' has a first rod or rod segment 174' and a second rod or rod segment 176'. The first rod 174' is characterized by a generally cylindrical rod body 178 formed of a suitable bio-compatible material of sufficient strength. The rod body 178 terminates at one end in a head 179. The second rod 176' is characterized by a generally cylindrical rod body 180 formed of a suitable bio-compatible material of sufficient strength. The rod body terminates at one end in a head 181. The heads 179, 181 of respective rods 174', 176' are received in coupling device 172'.

Figure 8:
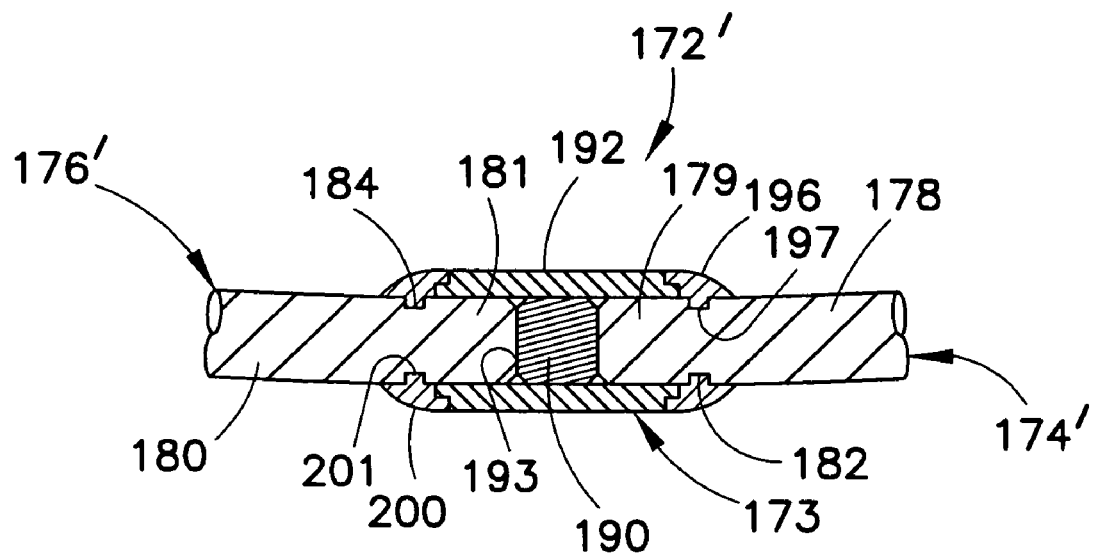
FIG. 8 is a sectional view of a portion of the dynamic spinal stabilization element of FIG. 7 taken along circle 8-8 thereof.
Figure 9:
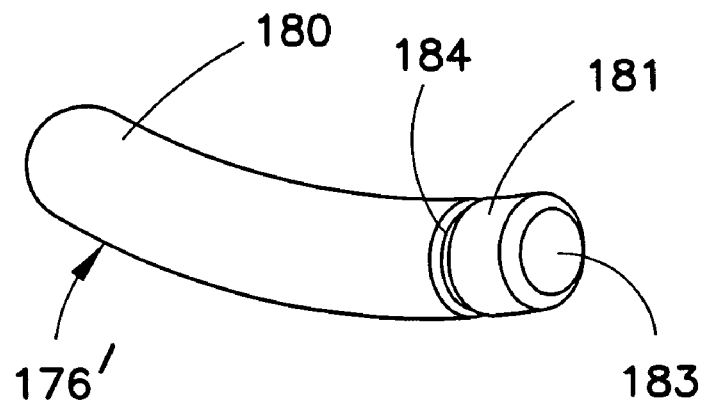
FIG. 9 is an enlarged, front perspective view of a rod of the dynamic spinal stabilization element of FIG. 7.

In FIG. 8, an enlargement of the coupling device 172' is shown. FIG. 9 is an enlargement of the end of the rod segment 176' since the end of the rod segment 174' is identical. The end of the rod segment 176' terminates in a head 181 defined in size by an annular groove 184. The head defines an end surface 183. Referring back to FIG. 8, the coupling device 172' is adapted to retain the ends 179, 181 of the respective rods 174', 176'. The coupling device 172' is formed by a membrane, sheath or the like 173. The membrane 173 is preferably, but not necessarily, formed of PEEK with a durometer that will allow for limited angulation (bending) or flexing relative to the rods.

The membrane 173 is formed by a middle portion 192 and first and second end portions 196, 200. The first end portion 196 has an annular ridge 197 on an inside surface thereof that is configured to receive the groove 182 of the head 179 of the rod body 178. The second end portion 200 has an annular ridge 201 on an inside surface thereof that is configured to receive the groove 184 of the head 181 of the rod body 180. An elastomeric spacer 190 is disposed between the end surfaces of the heads 179, 181 within the membrane 173. The coupling member 172' provides bending between the rods, but prevents axial movement of either rod.

Figure 10:
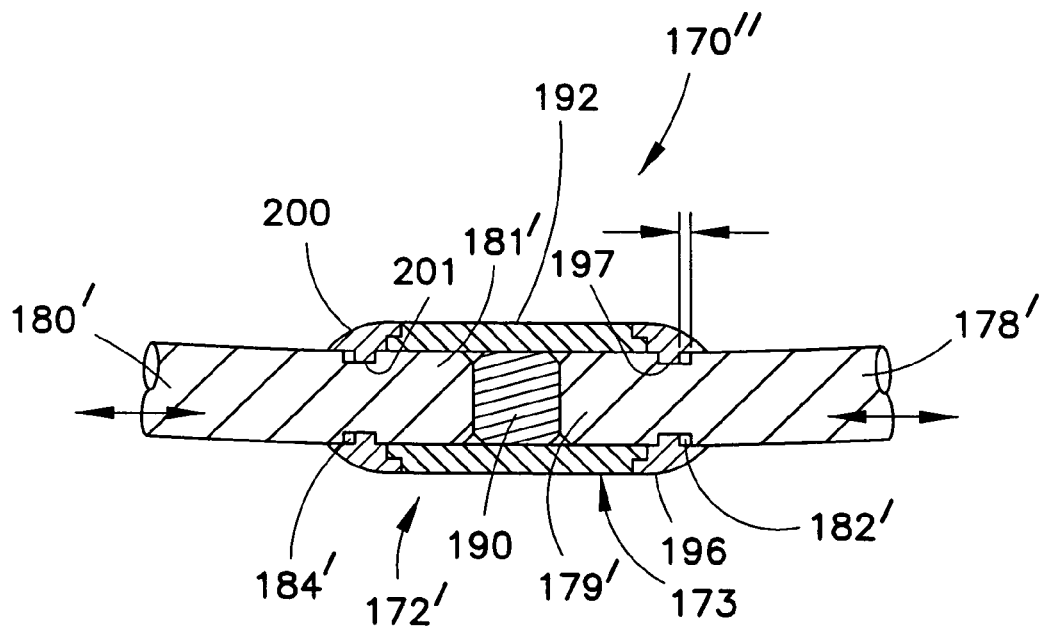
FIG. 10 is a sectional view of a portion of the dynamic spinal stabilization element in like manner to the sectional view of FIG. 8 depicting an alternative embodiment of a dynamic connection member of the dynamic spinal stabilization element of FIG. 7 that allows for axial translation.

Referring to FIG. 10, there is depicted a cross-sectional view of a portion of a form of the dynamic stabilization element 170' of FIG. 7, generally designated 170". The dynamic stabilization element 170" is identical to the dynamic stabilization element 170' with the exception of the rod segments. Particularly, a rod segment body 178' has a head 179' that is defined by an annular groove 182". The annular groove 182' is axially longer than the annular groove 182 of the rod body 178. This allows the rod body 178' to limitedly axially move relative to the membrane 173. The rod segment body 180' has a head 181' that is defined by an annular groove 184'. The annular groove 184' is axially longer than the annular groove 184 of the rod body 180. This allows rod body 180' to limitedly axially move relative to the membrane 173. The elastomeric spacer 190 provides limited compression for axial movement of the rods.

Figure 11:
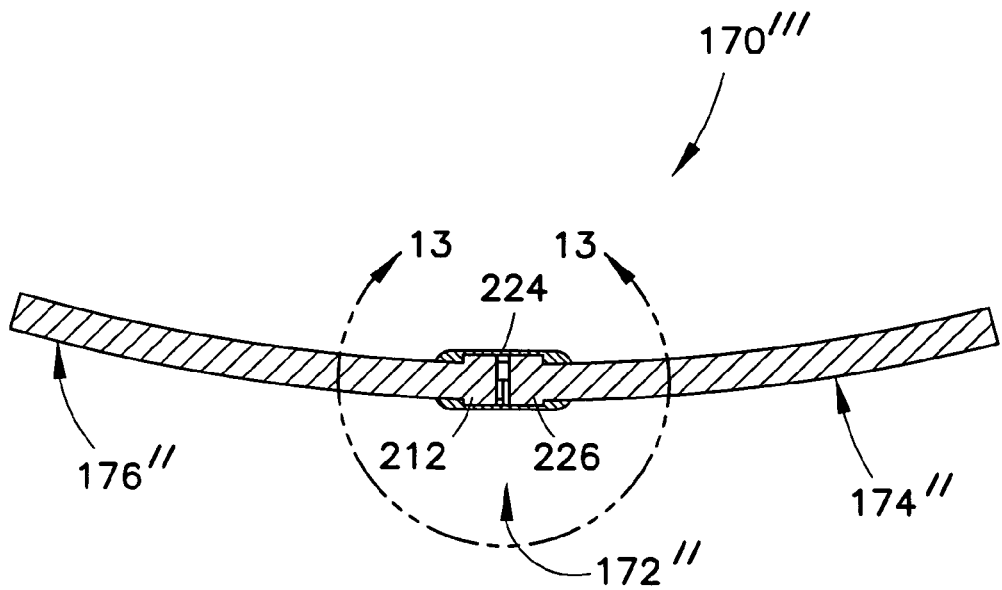
FIG. 11 is a sectional view of another form of the embodiment of the dynamic spinal stabilization element as shown in FIG. 6.

Referring to FIG. 11, there is depicted a cross-sectional view of another form of the dynamic stabilization element 170 of FIG. 6, generally designated 170'''. The dynamic stabilization element 170''' has a first rod or rod segment 174" and a second rod or rod segment 176". The first rod 174" is formed of a suitable bio-compatible material of sufficient strength and terminates at one end in a head 226. The second rod 176' is formed of a suitable bio-compatible material of sufficient strength and terminates at one end in a head 212. The heads 212, 226 are received in the coupling device 172".

Figure 12:
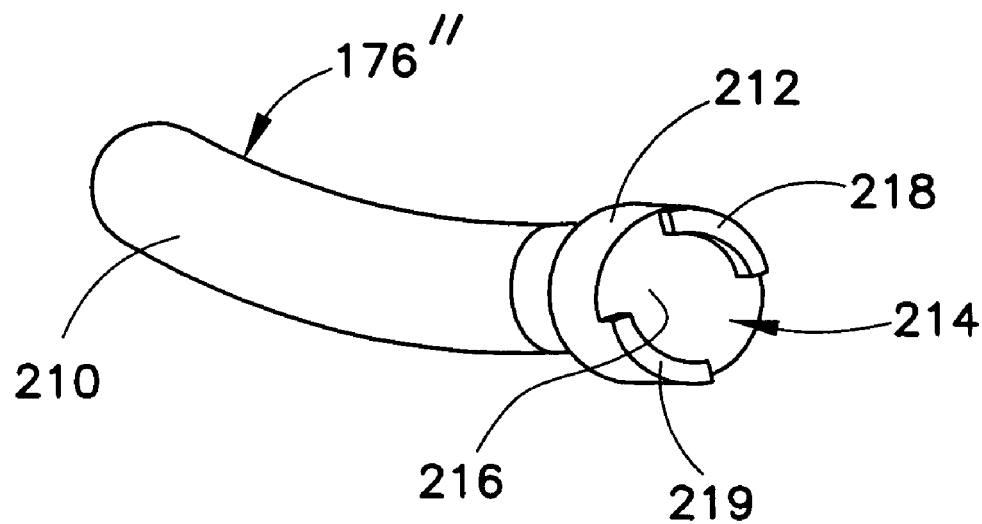
FIG. 12 is an enlarged, front perspective view of a rod of the dynamic spinal stabilization element of FIG. 11.

FIG. 12 is an enlargement of the rod segment 176" particularly of the head 212 thereof. The rod segments and thus the ends of the rod segments 174" and 176" are identical. The end of the rod segment 176" terminates in a head 212, the diameter of which may be larger than the diameter of the rod body. The head end 214 is defined by an end surface 214 and diametrically opposed, axially extending arcuate ridges, walls, or the like 218, 219 formed on an axial periphery of the end. The ridges 218, 219 form like open spaces between the ends thereof that are adapted to receive ridges 218, 219 of the rod segment 174". This provides a restricted rotation feature as between the rod segments 174", 176". Also, as the rods subside, or collapse upon each other, the rod segment join acting as one solid member, and no longer provide angulation or rotation. This is provided in various embodiments herein.

Figure 13:
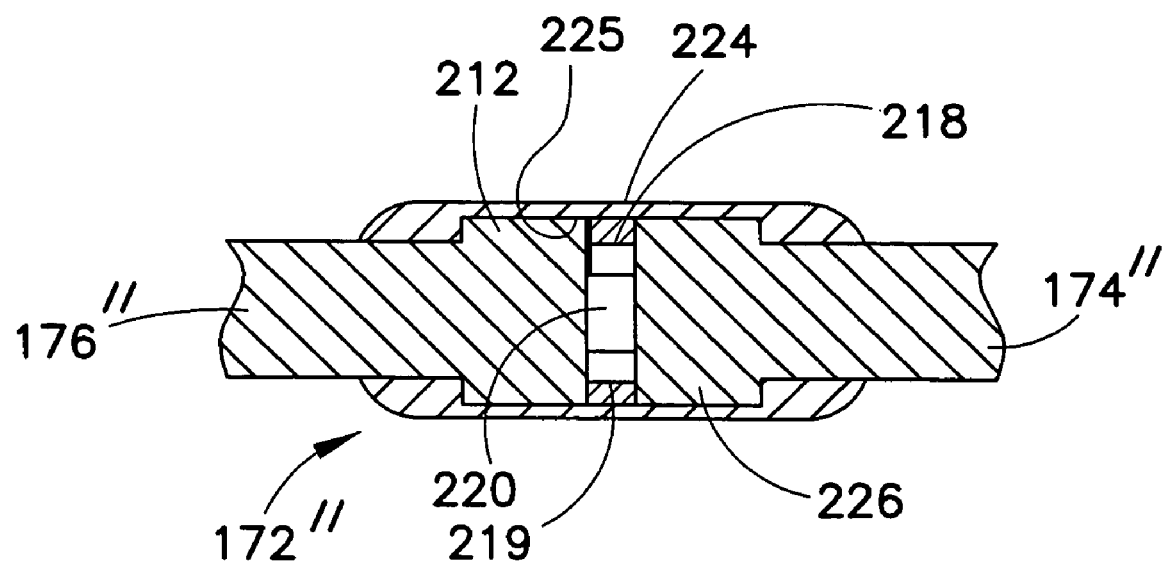
FIG. 13 is a sectional view of a portion of the dynamic spinal stabilization element of FIG. 11 taken along circle 13-13 thereof.

In FIG. 13, an enlargement of the coupling device 172" is shown. The coupling device 172" is adapted to retain the ends 212, 226 of the respective rods 176", 174". The coupling device 172" is formed by a one-piece membrane, sheath or the like 224. The membrane 224 is preferably, but not necessarily, formed of PEEK with a durometer that will allow for limited angulation (bending) or flexing relative to the rods. The membrane 224 is, in one form, over-molded on to the rod ends.

The membrane 224 defines an interior chamber 225 that receives the heads 212, 226. The rods 174", 176" are rotationally oriented relative to one another so as to interlock respective ridges 218, 219. The ridges 218, 219 also limit angulation.

Figure 14:
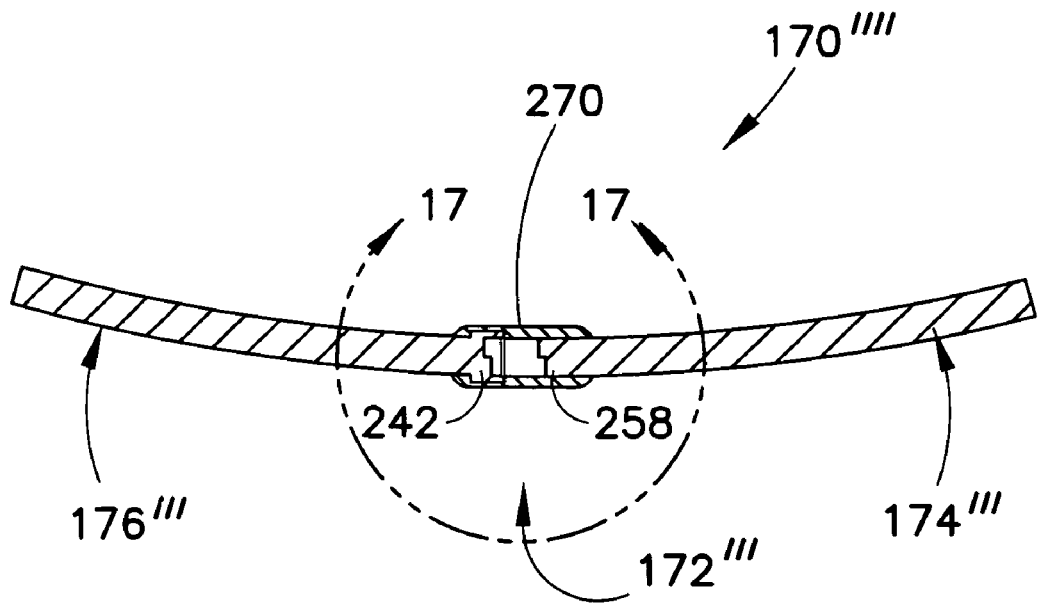
FIG. 14 is a sectional view of a further form of the embodiment of the dynamic spinal stabilization element as shown in FIG. 6.

Referring to FIG. 14, there is depicted a cross-sectional view of a further form of the dynamic stabilization element 170 of FIG. 6, generally designated 170"". The dynamic stabilization element 170"" has a first rod or rod segment 174''', a second rod or rod segment 176''' and a coupling device 172'''. The first rod 174''' is formed of a suitable biocompatible material of sufficient strength and terminates at one end in a head 242. The second rod 176''' is formed of a suitable bio-compatible material of sufficient strength and terminates at end 258 in a configured boss 260. The head 242 and configured boss 260 are received in the coupling device 172'''.

Figure 15:
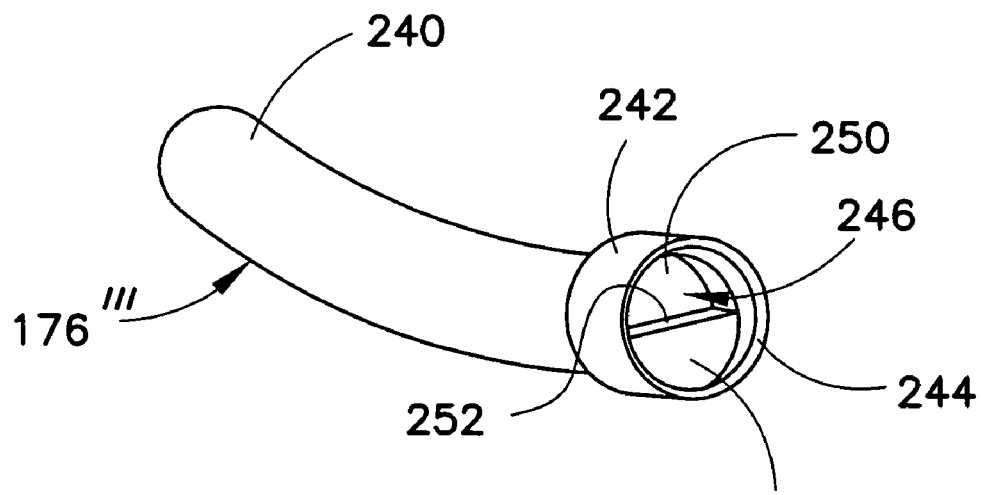
FIG. 15 is an enlarged, front perspective view of a rod of the dynamic spinal stabilization element of FIG. 14.

FIG. 15 is an enlargement of the rod segment 176''' particularly showing the head 242 thereof on the end of the rod body 240. The head 242 has a diameter that is larger than the diameter of the rod body 240. The head 242 defines an annular, peripheral rim 244 that defines an interior, cavity or recess 246. The recess 246 has a first surface 248 that is semicircular in shape, and a second surface 250 that is semicircular in shape. The second surface 250 is at a depth from the rim 244 that is greater than the depth of the first surface 248 so as to define a perpendicular ledge 252 therebetween.

Figure 16:
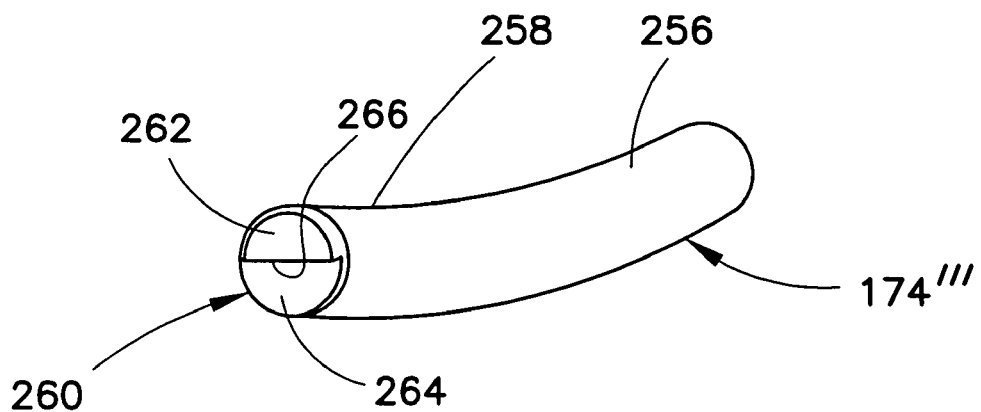
FIG. 16 is an enlarged, front perspective view of another rod of the dynamic spinal stabilization element of FIG. 14.

FIG. 16 is an enlargement of the rod segment 174''' particularly showing the end 258 of the rod body 256 and particularly the configured boss 260 thereof. The end 258 has a diameter that is the same as the diameter of the rod body 256. The boss 260 defines a semi-circular first surface 262, and a second semicircular surface 264. The first surface 262 is raised relative to the second surface 264 so as to define a perpendicular ledge 266 therebetween.

The rod ends are thus complementary providing an anti-rotation feature as between the rod segments 174", 176" when received in the coupling device. Particularly, the end 258 of the rod 174''' is received into head 242 of the rod 176''' such that the first surface 262 of the end 258 abuts or aligns with the second surface 250 of the head 242, while the second surface 264 of the end 258 abuts or aligns with the first surface 248 of the head 242. The ledges 252 and 266 also abut.

Figure 17:
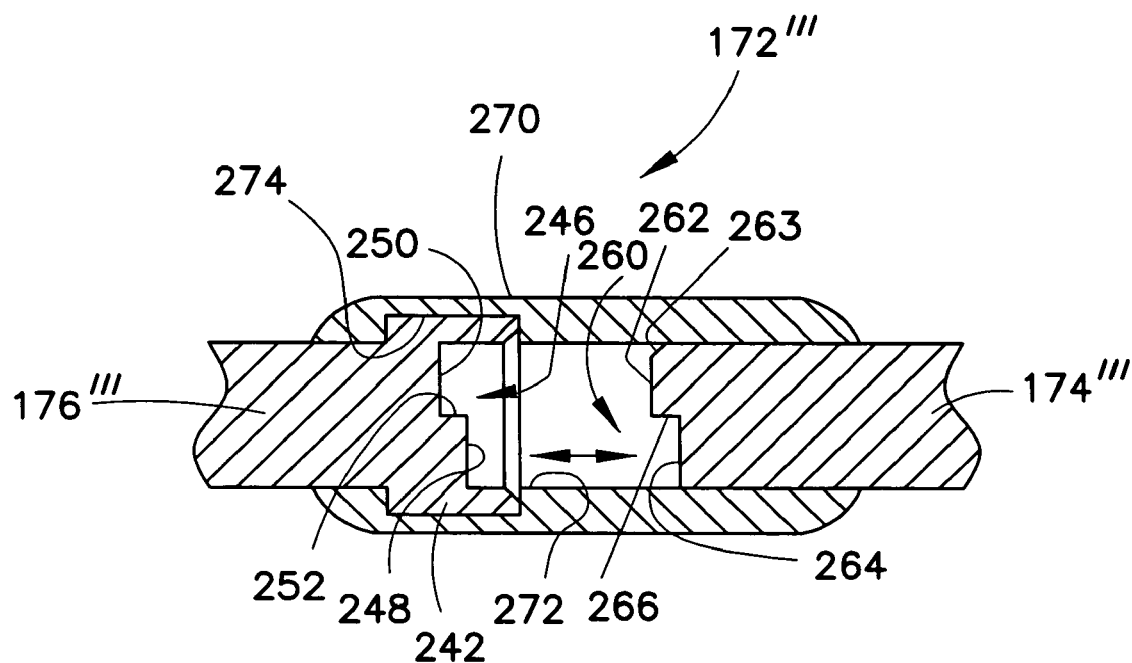
FIG. 17 is a sectional view of a portion of the dynamic spinal stabilization element of FIG. 14 taken along circle 17-17 thereof.

In FIG. 17, an enlargement of the coupling device 172''' is shown. The coupling device 172''' is adapted to retain the ends 242 and 258 of the respective rods 176''', 174'''. The coupling device 172''' is formed by a one-piece membrane, sheath or the like 270. The membrane 270 is preferably, but not necessarily, formed of PEEK with a durometer that will allow for limited angulation (bending) or flexing relative to the rods. The membrane 270 is, in one form, over-molded on to the rod ends.

The membrane 224 defines a first interior chamber 272 that is sized to overlay the end 258 and a second interior chamber 274 that is sized to overlay and retain the head 242. The rod 174''' is rotationally oriented relative to the rod 176''' so as to interlock. The rod 174''' is also limitedly axially movable relative to the coupling device 172''' and thus the rod 176'''.

Figure 18:
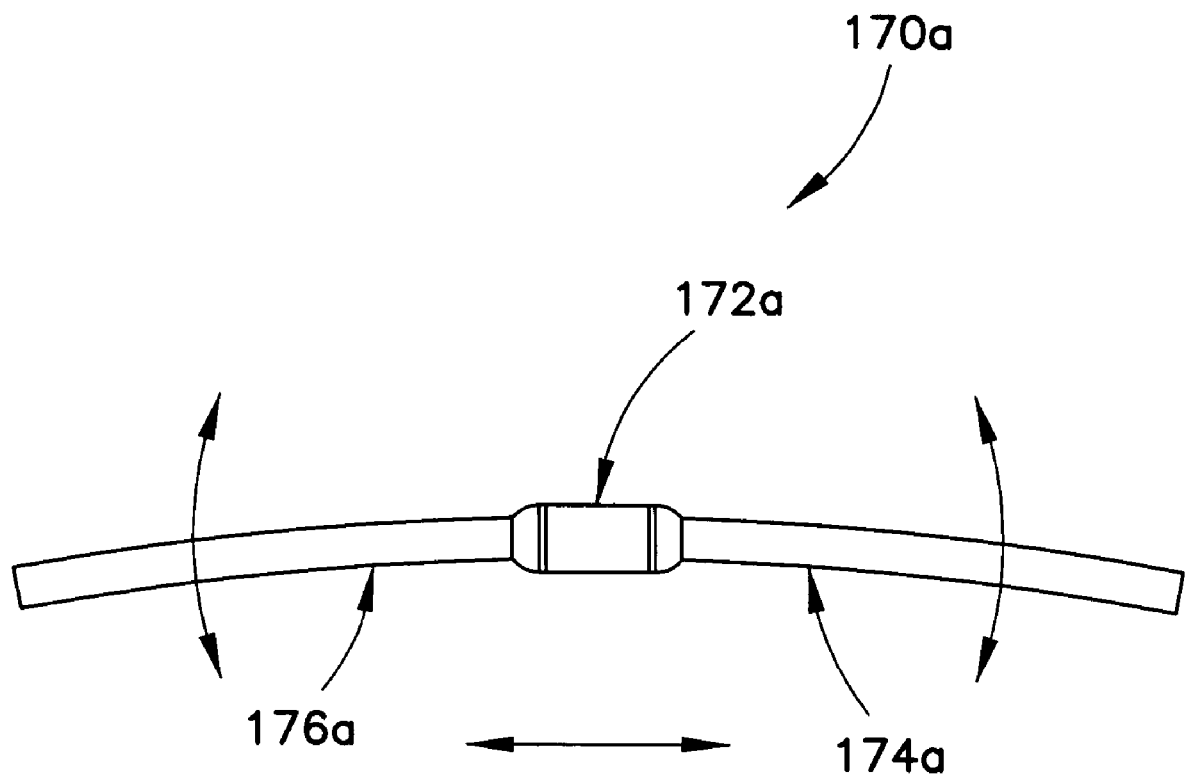
FIG. 18 is a side view of an embodiment of a dynamic spinal stabilization element fashioned in accordance with the present principles particularly depicting the direction and/or range of flexibility or motion thereof.

FIG. 18 depicts a general dynamic stabilization device 170a with rod segments 174a and 176a joined by coupling element 172a representing the various forms of the dynamic stabilization device 170. The double-headed arrows illustrate the manner of flex, bending or angulation, as well as axial movement where permitted, achieved by the dynamic stabilization device.

FIGS. 19-22 depict another embodiment of a dynamic spinal stabilization element or construct generally designated 400 especially for use in a spinal stabilization system or assembly. The dynamic spinal stabilization element 400 is a rod assembly that is designed to be retained at both ends to bone anchoring elements (see e.g. FIGS. 23-26) of a spine stabilization assembly. The dynamic spinal stabilization element 400 allows controlled motion, movement and/or bending relative to first and second rods or rod segments 402 and 404. The dynamic spinal stabilization element 400 provides a jointed spinal rod having controllable degrees of freedom or bending (compression-distraction).

The first rod segment 402 is formed of a bio-compatible material of a suitable material strength such as titanium and is characterized by a generally tubular body 403 of any appropriate length and/or diameter. The second rod segment 404 is formed of a bio-compatible material of a suitable material strength such as titanium and is characterized by a generally tubular body 405 of any appropriate length and/or diameter.

The dynamic spinal stabilization element 400 has a coupling element 408 that provides jointed coupling or attachment of the rod segments 402 and 404. The coupling element 408 is formed of a bio-compatible material of a suitable low durometer such as PEEK or a carbon fiber reinforced PEEK. The coupling element 408 may also be metal such as titanium. The coupling element 408 is formed of a plurality of rings here shown as a center ring 408 having curved faces that form a frusto-conical cross section, first right and left adjacent rings 432 and 434 each having concentric curved faces, second right and left adjacent rings 436 and 438 each having concentric curved faces, and third right and left adjacent rings 440 and 442 each having concentric curved faces. More or less adjacent rings may be provided.

The dynamic spinal stabilization element 400 also includes a spring rod 406 made from a hardened titanium (e.g. 6AL4VELI) for providing a spring temper and having a rod body 410 that extends through the rod segments 402 and 404. The spring rod 406 has a head 412 that is sized to abut the end of the rod segment 402 and an externally threaded tip 414. An internally threaded nut 420 is provided on the threaded tip 414. The nut 420 includes a stop 422 that abuts an end 415 of the tip 414. Adjustment of the nut 420 changes the amount of dynamization of the element 400. Particularly, as the nut is tightened, the head 412 presses against the end of the rod segment 402 to provide compression. The more compression the less degrees of freedom of dynamization. As the nut is loosened, there is less compression and more degrees of freedom of angulation. Moreover, as the nut is loosened, the spring rod will carry the load and the adjacent rings (coupling element 408) act as stops for angulation. The adjacent rings may also aid in preventing stress risers on the spring rod.

The dynamic spinal stabilization element 400 can come in lordosed and straight versions. Sizes can vary but exemplary sizes are 5.5 mm and 6.35 mm. There can also be one (1) through three (3) levels available with static and dynamic combinations. Rings or spacers of the connector can be added of an elastomeric compound that provides for movement (dynamization) as described.

Figure 23:
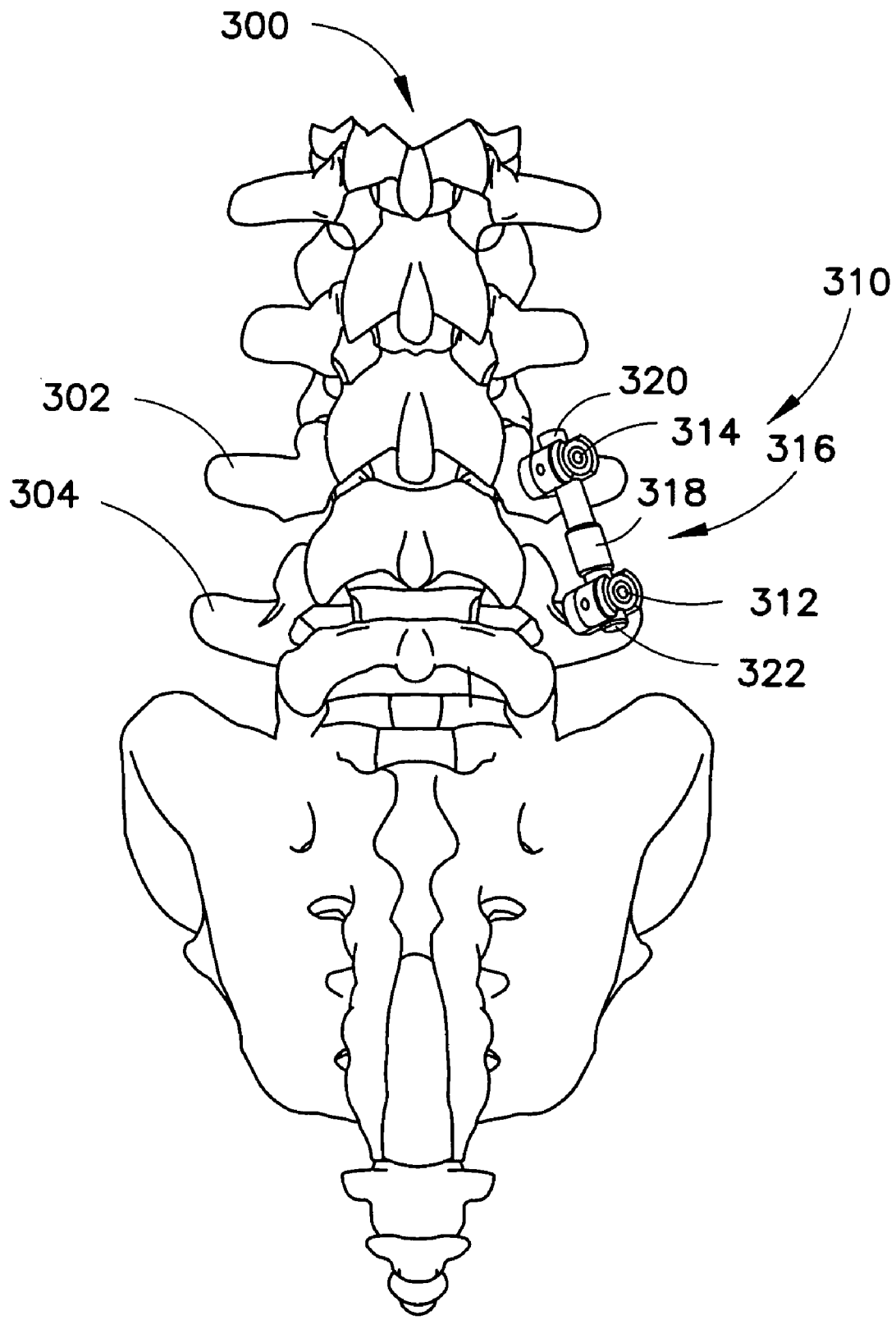
FIG. 23 is a posterior view of a portion of a spinal column having a spinal stabilization system affixed to adjacent vertebrae and utilizing a linear dynamic spinal stabilization element of the present invention.
Figure 24:
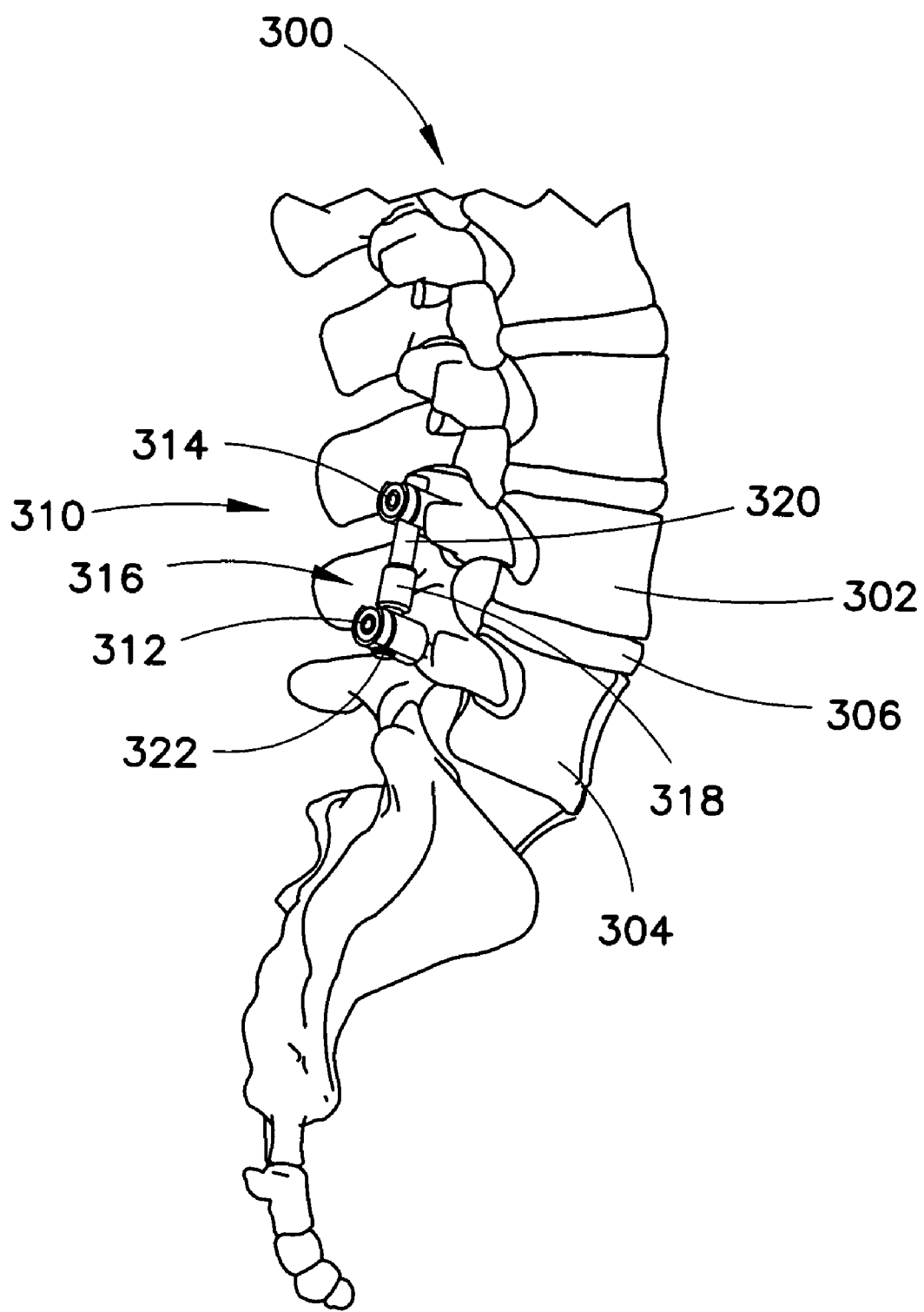
FIG. 24 is a side view of the portion of the spinal column of FIG. 23 depicting use of the linear dynamic spinal stabilization element.

FIGS. 23 and 24 depict a portion of a spinal column 300 (lower lumbar) to which is attached a dynamic stabilization assembly 310 utilizing a present dynamic stabilization element 316 representing any one of the present dynamic rod structures. Particularly, a first bone anchoring device 312 of the dynamic stabilization assembly 310 is attached to a first vertebra 304, while a second bone anchoring device 314 of the dynamic stabilization assembly 310 is attached to a second, adjacent vertebra 302. A first straight rod segment 322 is retained by the first bone anchoring device 312 while a second straight rod segment 320 is retained by the second bone anchoring device 314. The two straight rod segments 320, 322 are joined by a dynamic coupling element 318.

Figure 25:
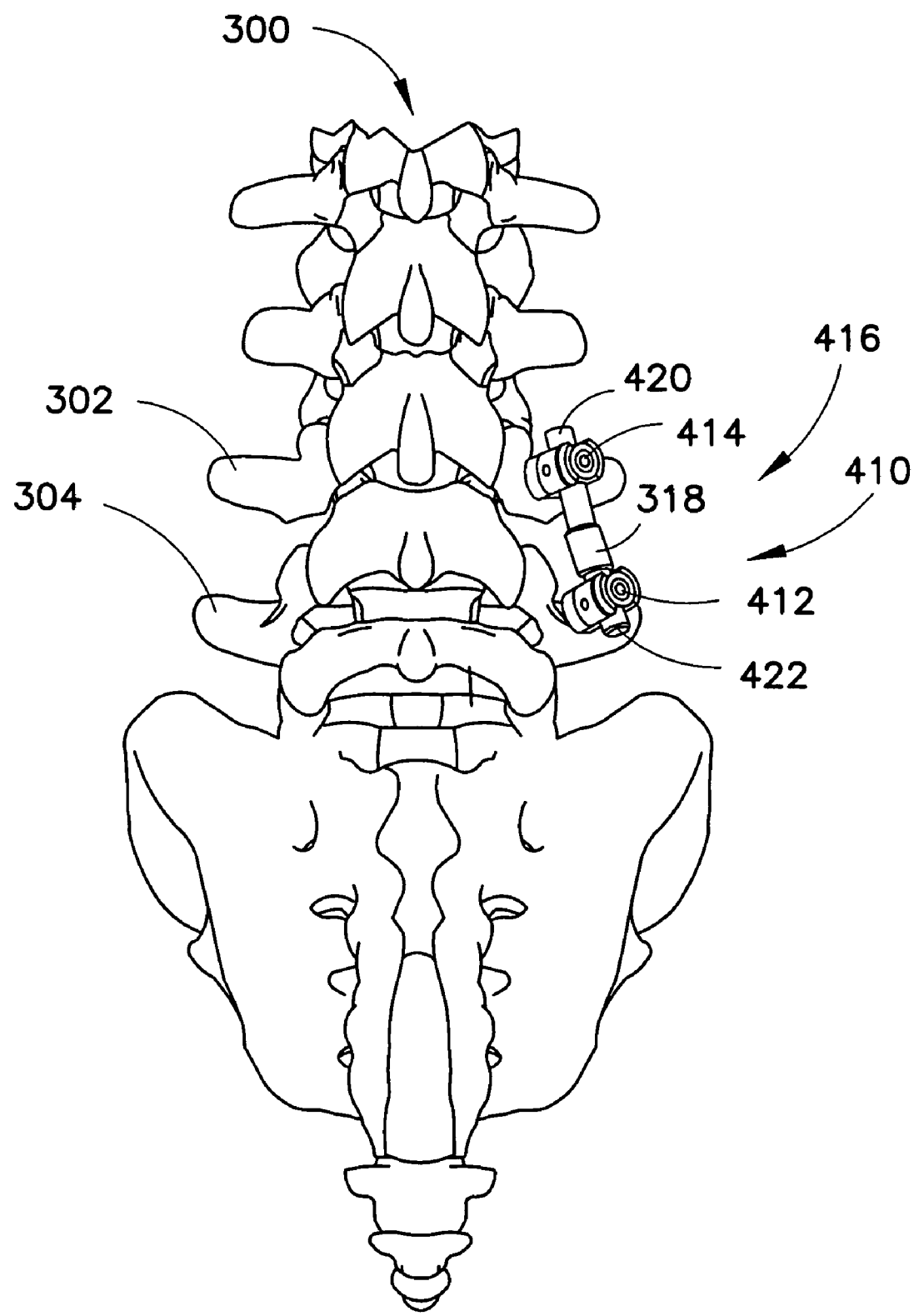
FIG. 25 is a posterior view of a portion of a spinal column having a spinal stabilization system affixed to adjacent vertebrae and utilizing a curved dynamic spinal stabilization element of the present invention.
Figure 26:
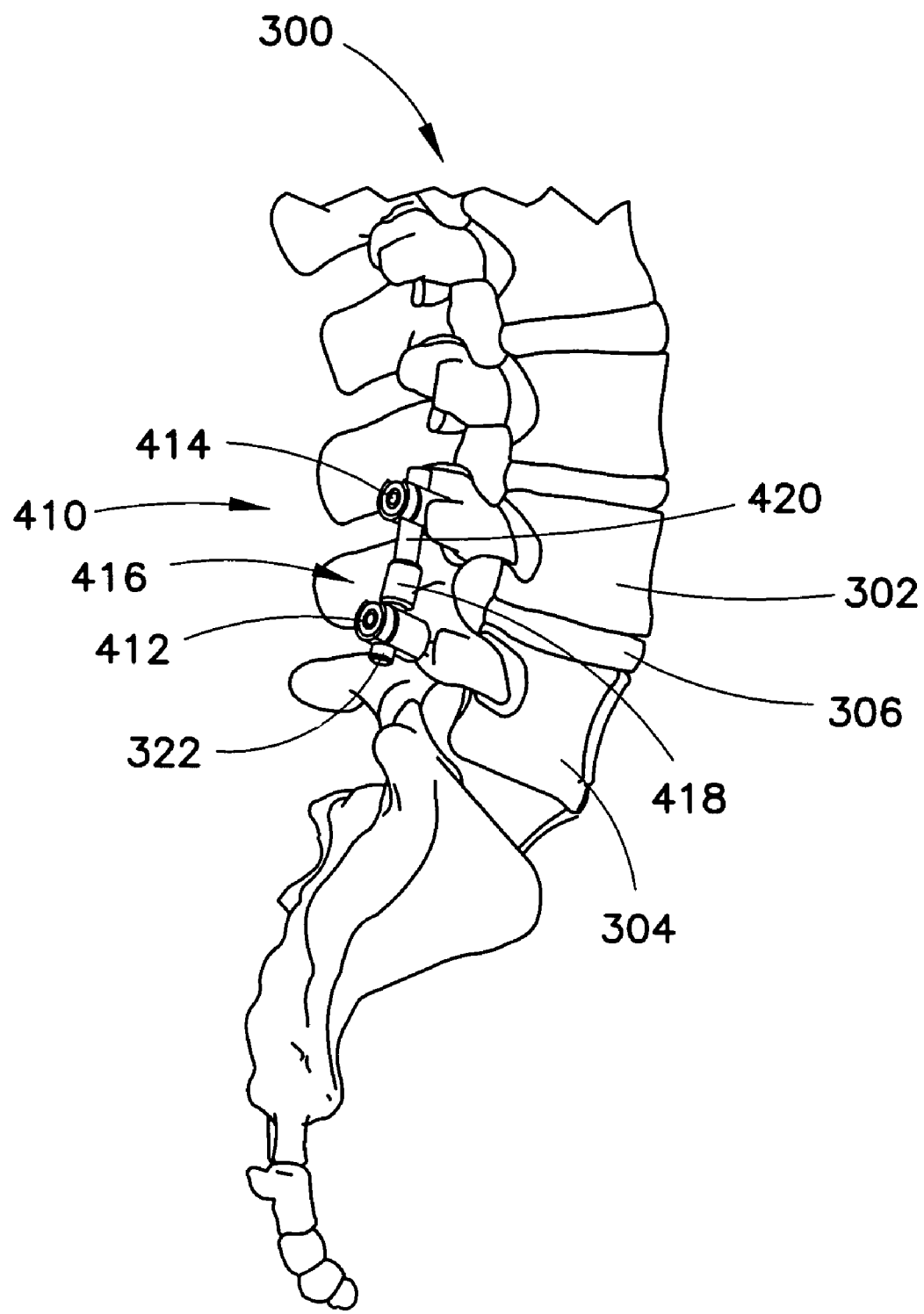
FIG. 26 is a side view of the portion of the spinal column of FIG. 25 depicting use of the curved dynamic spinal stabilization element.

FIGS. 25 and 26 depicted the lower portion of the spinal column 300 to which is attached another dynamic stabilization assembly 410 utilizing a present dynamic stabilization element 416 representing any one of the present dynamic rod structures. Particularly, the first bone anchoring device 412 of the dynamic stabilization assembly 410 is attached to a first vertebra 304, while a second bone anchoring device 414 of the dynamic stabilization assembly 410 is attached to a second, adjacent vertebra 302. A first curved rod segment 422 is retained by the first bone anchoring device 412 while a second curved rod segment 420 is retained by the second bone anchoring device 414. The two curved rod segments 420, 422 are joined by a dynamic coupling element 418.

It should be appreciated that the rod segments can be embodied in a multi-level format. Dynamic stabilization assemblies according to the present invention may also include more than one connector. One or more of the present dynamic stabilization assemblies allow for in-situ adjustability. Such in-situ adjustment can limit flexion, extension, rotation and translation (subsidence).

It should also be appreciated that the above description is only exemplary of the principles of the subject invention. Therefore, other embodiments are contemplated and within the present scope.

It should moreover be appreciated that the present invention can be further modified within the spirit and scope of this disclosure. This application is therefore intended to cover any variations, uses, of adaptations of the invention using its general principles. Further, this application is intended to cover such departures from the present disclosure as come within known or customary practice in the art to which this invention pertains.

What is claimed is:

1. A dynamic spine stabilization element comprising:
a first rod segment having a tubular body;
a second rod segment having a tubular body;
a coupling element that couples the first rod segment and the second rod segment, the coupling element comprises:
a center ring having a frusto-conical cross-section with concentric axially-disposed faces;
a first pair of rings, each having concentric axially-disposed inner and outer faces, the inner faces of the first pair of rings engage the concentric axially-disposed faces of the center ring;
a spring rod extending through the tubular bodies of the first and second rod segments, and the coupling element;
an adjustment device coupled to the rod to allow in-situ adjustability of dynamization of the first and second rod segments by axial compression of the first rod segment, second rod segment, and the rings or the coupling element.

2. The dynamic spine stabilization element of claim 1, wherein the in-situ-adjustability of dynamization of the first and second rod portions limits flexion, extension, rotation, and/or translation of the first and second rod portions.

3. The dynamic spine stabilization element of claim 1, wherein the adjustment device comprises a nut threaded onto an end of the spring rod so that adjustment of the nut changes the amount of dynamization of the dynamic spine stabilization element.

4. The dynamic spine stabilization element of claim 1, wherein the coupling element further comprising:
a second pair of rings, each having concentric axially-disposed inner and outer faces, the inner faces of the second set of rings engage the concentric outer faces on the first pair of rings;
a third pair of rings, each having concentric axially-disposed inner and outer faces, the inner faces of the third set of rings engage the concentric outer faces on the second pair of rings.

5. The dynamic spine stabilization element of claim 4, wherein the first rod segment has an annular face that engages the outer face of one of the third pair of rings, and the second rod segment has an annular face that engages the outer face of the other of the third pair of rings.

6. A dynamic spine stabilization element comprising:
a first rod segment having a tubular body;
a second rod segment having a tubular body;
a coupling element that couples the first rod segment and the second rod segment, the coupling element comprises:
a center ring having a frusto-conical cross-section with concentric axially-disposed planar faces;
a first pair of rings, each having concentric axially-disposed inner and outer planer faces, the inner planer faces of the first pair of rings engage the concentric axially-disposed planer faces of the center ring;
a spring rod extending through the tubular bodies of the first rod segment, the second rod segment, and the coupling element;
an adjustment device coupled to the rod to allow in-situ adjustability of dynamization of the first and second rod segments by axial compression of the first rod segment, second rod segment, and the rings or the coupling element.

7. The dynamic spine stabilization element of claim 6, wherein the coupling element further comprising:
a second pair of rings, each having concentric axially-disposed inner and outer planar faces, the inner planar faces of the second set of rings engage the concentric outer planar faces on the first pair of rings;
a third pair of rings, each having concentric axially-disposed inner and outer planar faces, the inner planar faces of the third set of rings engage the concentric outer planar faces on the second pair of rings.

8. The dynamic spine stabilization element of claim 7, wherein the first rod segment has an annular planar face that engages the outer planar face of one of the third pair of rings, and the second rod segment has an annular planar face that engages the outer planar face of the other of the third pair of rings.

9. The dynamic spine stabilization element of claim 8, wherein the adjustment device comprises a nut threaded onto an end of the spring rod so that adjustment of the nut changes the amount of dynamization of the dynamic spine stabilization element.

* * * * *